United States Patent
Lozupone et al.

(10) Patent No.: US 8,097,407 B2
(45) Date of Patent: Jan. 17, 2012

(54) METASTATIC HUMAN TUMOR ASSOCIATED MOLECULE, METHODS TO DETECT BOTH ACTIVATED GENE AND PROTEIN AND TO INTERFERE WITH GENE EXPRESSION

(75) Inventors: Francesco Lozupone, Rome (IT); Stefano Fais, Rome (IT)

(73) Assignee: Hansabiomed OU, Tallin (EE)

( * ) Notice: Subject to any disclaimer, the term of this patent is extended or adjusted under 35 U.S.C. 154(b) by 82 days.

(21) Appl. No.: 12/321,821

(22) Filed: Jan. 26, 2009

(65) Prior Publication Data

US 2009/0191222 A1    Jul. 30, 2009

Related U.S. Application Data

(60) Provisional application No. 61/062,453, filed on Jan. 25, 2008.

(51) Int. Cl.
- *C12Q 1/68* (2006.01)
- *G01N 33/53* (2006.01)
- *G01N 33/574* (2006.01)

(52) U.S. Cl. .............................. 435/6; 435/7.1; 435/7.23

(58) Field of Classification Search ........................ None
See application file for complete search history.

(56) References Cited

U.S. PATENT DOCUMENTS

2003/0008356 A1 * 1/2003 Fukushima et al. ......... 435/69.1

FOREIGN PATENT DOCUMENTS

WO    WO 2006110593 A2 * 10/2006

OTHER PUBLICATIONS

Lugini L. et al. 2003. Potent phagocytic activity discriminates metastatic and primary human malignant melanomas: a key role of ezrin. Lab. Investigation 83(11): 1555-1567.

Lugini L. et al. 2006. Cannibalism of live lymphocytes by human metastatic but not primary melanoma cells. Cancer Res 66(7): 3629-3638.

* cited by examiner

*Primary Examiner* — Anne M. Gussow

(74) *Attorney, Agent, or Firm* — Gearhart Law, LLC

(57) ABSTRACT

This disclosure characterizes the function and the expression of the human protein encoded by tm9sf4. The protein is highly expressed in malignant tumor cells and therefore is a novel marker for malignancy. Moreover, the protein is involved in the phagocytotic character of tumor cells. This disclosure provides methods and tools to diagnose and follow up malignancy of tumors. Furthermore, means to inhibit phagocytotic character of tumor cells as well as means to treat cancer are provided.

Figure 1:
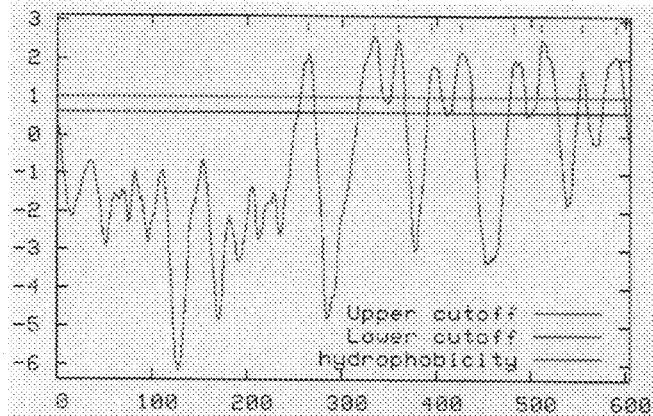
Figure 1:
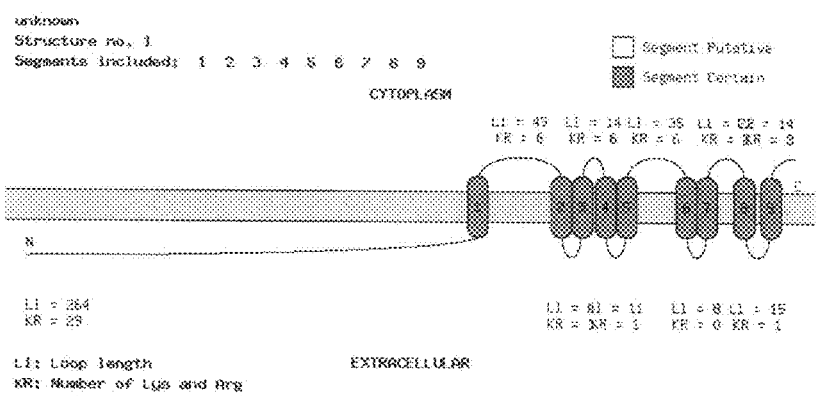

9 Claims, 10 Drawing Sheets
(7 of 10 Drawing Sheet(s) Filed in Color)

METASTATIC HUMAN TUMOR ASSOCIATED MOLECULE, METHODS TO DETECT BOTH ACTIVATED GENE AND PROTEIN AND TO INTERFERE WITH GENE EXPRESSION

PRIORITY

This application claims priority of the U.S. Provisional application No. 61/062,453 which was filed on Jan. 25, 2008.

SEQUENCE DATA

This application contains sequence data provided on a computer readable diskette and as a paper version. The paper version of the sequence data is identical to the data provided on the diskette.

FIELD OF THE INVENTION

The present invention relates generally to the field of cancer research and more specifically to identification of new tumorigenesis and metastasis related proteins and genes. The invention relates to a new marker of malignancy. The invention further relates to the field of gene therapy.

BACKGROUND OF THE INVENTION

In 2005, 7.6 million people died of cancer out of 58 million deaths worldwide. Based on projections, cancer deaths will continue to rise with an estimated 9 million people dying from cancer in 2015, and 11.4 million dying in 2030 (WHO data). Cancer treatment may involve surgery, radiation therapy, chemotherapy, hormonal therapy, or some combination of these, but presently survival rates for the most of cancer patients is very low. According to World Health Organization, one third of the cancer burden could be cured if detected early and treated adequately. Pathological research provides means for establishing the diagnosis of the most of solid tumors. Although many cases can be classified reliably with current pathological criteria, there is a significant subset of cases in which no consensus can be reached even among expert pathologists. Diagnostic ambiguity has significant adverse consequences for patients. Misclassifying a tumor as benign may be fatal, and diagnosing a benign lesion as malignant may result in significant morbidity. Currently there is no method to definitively resolve these ambiguities. Therefore, there is a clear need for a diagnostic test that could reduce these uncertainties.

Phagocytosis is the process by which cells internalize large particles (typically 0.1 mm diameter), such as bacteria or cell debris. The early stage of phagocytosis can be tentatively divided into distinctive steps: cell membrane binding around the particle, phagosome formation, and internalization of the phagosome. In the process of phagosome formation and internalization, actin cytoskeleton has been proposed to drive these steps to allow engulfment.

Phagocytic cells have been identified in malignant tumors up to a century ago, and, more recently, cells with phagocytic behavior (also defined as cannibalistic behavior) have been detected in tumors of different histology, such as oat cell carcinoma of the lung, breast cancer, bladder cancer, medulloblastoma, gastric adenocarcinomas, melanoma and squamous cell carcinoma of the skin.

We have recently observed that phagocytosis is a character of metastatic melanoma cells able to phagocytose apoptotic cells, plastic beads stained yeasts, and live lymphocytes displaying efficient phagocytic machinery responsible for a macrophage-like activity, while melanoma cells derived from primary lesions did not display any cannibalistic or phagocytic activity. Moreover, cannibal cells can be detected in 100% metastatic melanoma lesions (Lugini et al., 2004; Lugini et al., 2006).

One of the main features of cannibal cells is an increased acidity of lysosomal-like vesicles and an over expression of cathepsin B, a proteolytic enzyme reported to be involved in tumor invasion and metastasis (Sloane et al., 1981). Differently from professional phagocyte-like macrophages, cannibal tumor cells do not utilize structures like ruffles or any pseudopodial movement. Instead, live or dead material that touches the tumor cell's external membrane is immediately endocytosed and digested through a sort of quicksand mechanism that seems not to involve any specific receptor.

These findings have led us to speculate that cannibal cells feed of other cells, perhaps with no particular need of blood-derived nutrient supply, but also that cannibalism of lymphocytes by tumor cells may represent a rudimentary mechanism of tumor immune escape. Moreover, these findings led us to a novel, revolutionary interpretation that cancer cells, in their habit to use other cells for feeding, may behave as unicellular eukaryotes whose unique purpose is to survive in a continuous fighting against other cells and the unfavourable environment. This theory further led us to speculate that amoebas and metastatic cells might share the same framework with the same regulatory elements allowing their surviving in adverse micro-environmental conditions. However, so far no genes have ever been specifically associated with the cannibal behaviour of cancer cells.

The cellular slime mold *Dictyostelium discoideum* has been previously used as a model organism to study phagocytosis. Mechanisms involved in phagocytosis by *Dictyostelium* cells are very similar to those used by mammalian phagocytes, and involve the actin cytoskeleton and RacF1, a member of the Rho family of GTPbinding proteins. However, no phagocytosis associated specific proteins have ever been identified in mammals.

It has been recently found that the protein encoded by PHG1A gene was implicated in cell adhesion and phagocytosis in the amoeba *Dictyostelium discoideum*. This protein belongs to TM9 superfamily and genes encoding TM9 proteins can be unambiguously identified in eukaryotic genomes. The family includes many members in organisms ranging from yeast to plants and human. To mention some example, there are three members of this family in *Saccharomyces cerevisiae, Dictyostelium* amoebae, and *Drosophila* flies and four in humans and mice. All of them exhibit a similar overall structure, with a rather variable potential luminal domain followed by a more conserved membrane domain and nine or ten putative transmembrane domains.

SUMMARY OF THE INVENTION

Based on our theory that cancer cells use other cells for feeding and behaving as unicellular eukaryotes and possibly share the same framework with the same regulatory elements as amoebas, we compared PHG1A gene with human genome. Three homologues of phg1 have been fully sequenced in human (TM9SF4, U81006 and U94831), and we found the closest homologue of phg1 of *Dictyostelium dicoideum* in human to be tm9sf4 (other aliases: KIAA0255, dJ836N17.2) locating in chromosome 20q11.21. Even if this gene is fully sequenced, its function or expression product of this has never been characterized.

Accordingly, we have studied the function and the expression of the protein encoded by tm9sf4 in more details. In this disclosure, we show the function of the protein and provide a number of applications.

This disclosure shows that the protein is highly expressed in malignant cells. Observations on several melanoma cell lines deriving from patients show that TM9SF4 is a marker of malignancy, since this protein is undetectable on the cell lines deriving from primary lesions. Furthermore, this protein is involved in the phagocytic behavior of metastatic melanoma cells, since silencing the gene encoding this protein strongly inhibits the phagocytic behavior of metastatic cells. Based on these observations we have named this protein as TUCAP-1 (Tumor associated cannibal protein 1). The gene coding for this protein is here accordingly called tucap-1 gene.

This invention addresses the need for a rapid test to detect malignant cells and diagnose melanoma and other tumors. Accordingly, this disclosure provides antibodies, primers, oligopeptides and polypeptides useful for TUCAP-1 detection, analysis and potential therapeutic effects.

This invention provides polynucleotides corresponding or complementary to all or part of the tucap-1 gene, and polynucleotides or oligonucleotides, which hybridize to the tucap-1 gene, mRNAs, or to TUCAP-1-encoding polynucleotides. Recombinant DNA molecules containing TUCAP-1 polynucleotides, cells transformed or transduced with such molecules, and host-vector systems for the expression of tucap-1 gene products are provided. The disclosure further provides TUCAP-1 protein and polypeptide fragments thereof.

The invention further provides antibodies that bind to TUCAP-1 proteins and polypeptide fragments thereof, including polyclonal and monoclonal antibodies, murine and other mammalian antibodies, chimeric antibodies, humanized and fully human antibodies, and antibodies labelled with a detectable marker, and antibodies conjugated to radionucleotides, toxins or other therapeutic compositions. The invention further provides methods for detecting the presence of TUCAP-1 polynucleotides and proteins in various biological samples, as well as methods for identifying cells that express TUCAP-1.

SHORT DESCRIPTION OF THE DRAWINGS

The patent application file contains at least one drawing executed in color. Copies of this patent or patent application publication with color drawings will be provided by the Office upon request and payment of the necessary fee.

FIG. 1 Molecular structure of TM9SF4/TUCAP-1 protein.

(A) Hydropathy profile of TUCAP-1 protein sequence. Hydrophobic regions are indicated above the line by positive values. Amino acid numbering is indicated on the abscissa. Hydrophilic stretch in the N-terminal region is followed by nine hydrophobic regions. Analysis was performed according to Claros and von Heijneb using TopPred prediction Program.

(B) Graphic representation of TUCAP-1 secondary structure according to TopPred predictor server.

Figure 2:
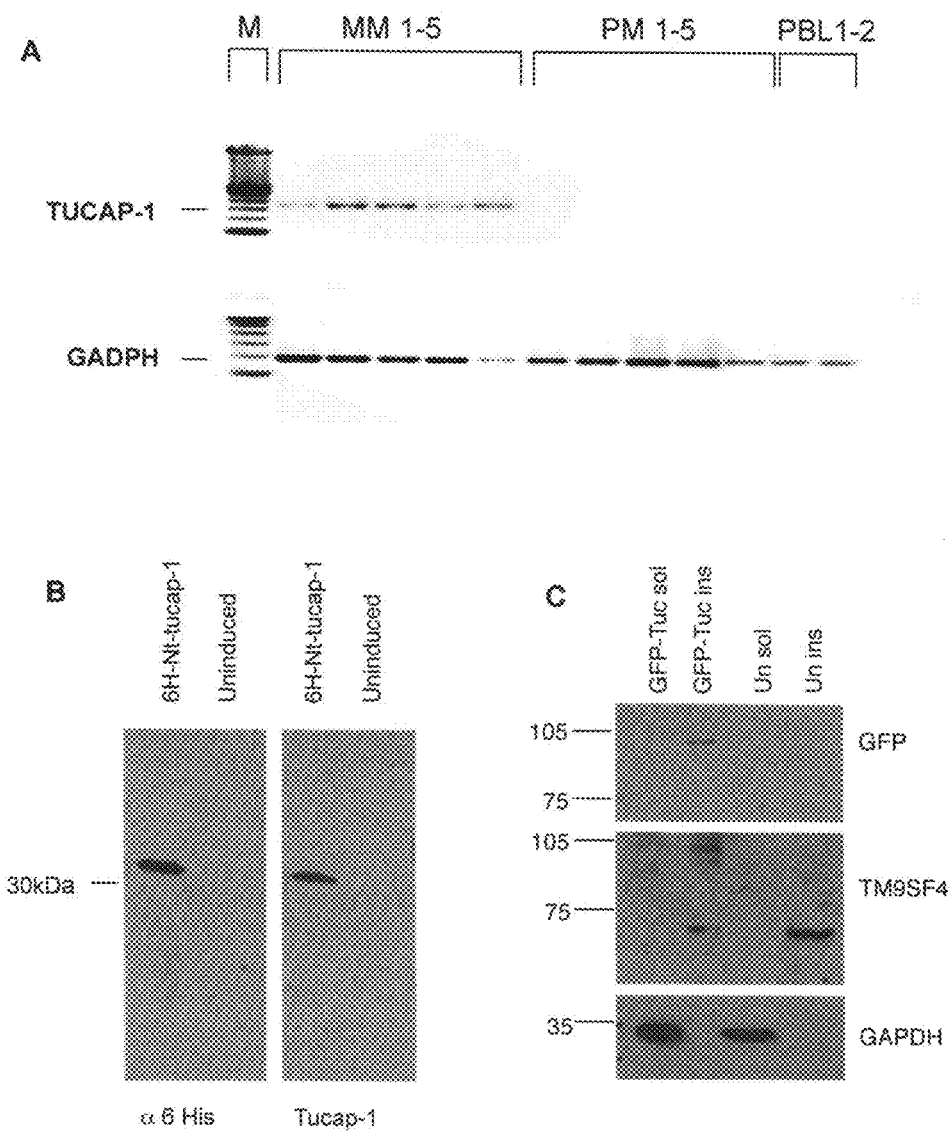

FIG. 2. Detection of TM9SF4/TUCAP-1 transcripts and characterization of TUCAP-1 antibodies (A) RT-PCR analysis of TUCAP-1 (upper panel) and GAPDH (lower panel) on five metastatic (MM1-5) and five primary melanoma (PM1-5) cell lines recently established in vitro from metastatic lesion, and peripheral blood cells from two different donors (PBL1-2); M size marker.

(B) Western blots of 6-histidine or TUCAP-1 in the six-histidine tagged TUCAP-1 peptide used to immunize mice and in uninduced bacterial lysates. Equal amount of purified protein and bacterial lysate was loaded on reducing gels and blotted with the 6-His-antibody or TUCAP-1 mice antisera. Proteins were visualized using HRP-conjugated secondary antibodies and revealed with ECL system (Pierce).

(C) Western blotting for GFP-TUCAP-1 and GAPDH on Triton soluble (lane 1) and Triton insoluble (lane 2) fractions of GFP-TUCAP-1 (GFP-Tuc) transfected MM 1 cells, and Triton soluble and insoluble fractions of untransfected MM1 cells (lanes 3-4). M size marker. Proteins were visualized using HRP conjugated secondary antibodies and revealed with ECL (Pierce). As molecular weight markers Rainbow™ (Amersham UK) prestained standards were used.

Figure 3:
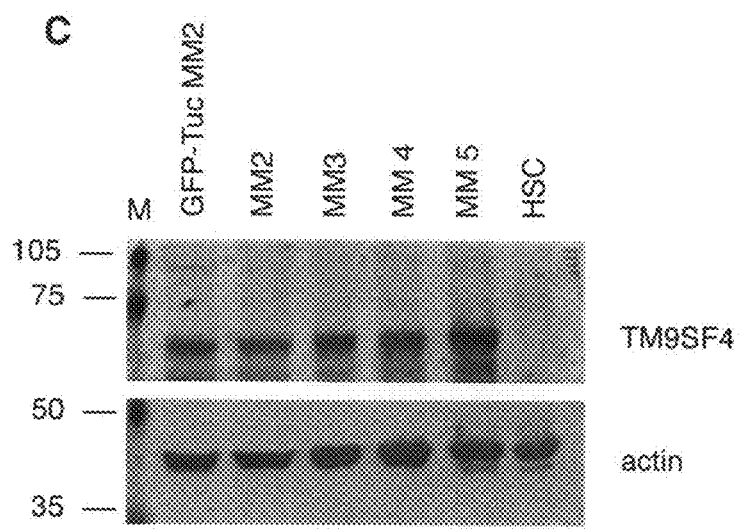

FIG. 3. Western blotting analysis of TUCAP-1

Western blotting for TUCAP-1 detection on GFP-Tuc Transfected MM2 cells, Four metastatic melanoma cell lines (MM2-5), and CCD-1064SK human skin fibroblasts (HSC). Loading amount was controlled by immunodetection of actin. Proteins were visualized using HRP conjugated secondary antibodies and DAB system (DAKO, Denmark) as cromogen. Rainbow™ (AmershamUK) prestained standards were used as molecular weight markers.

Figure 4:
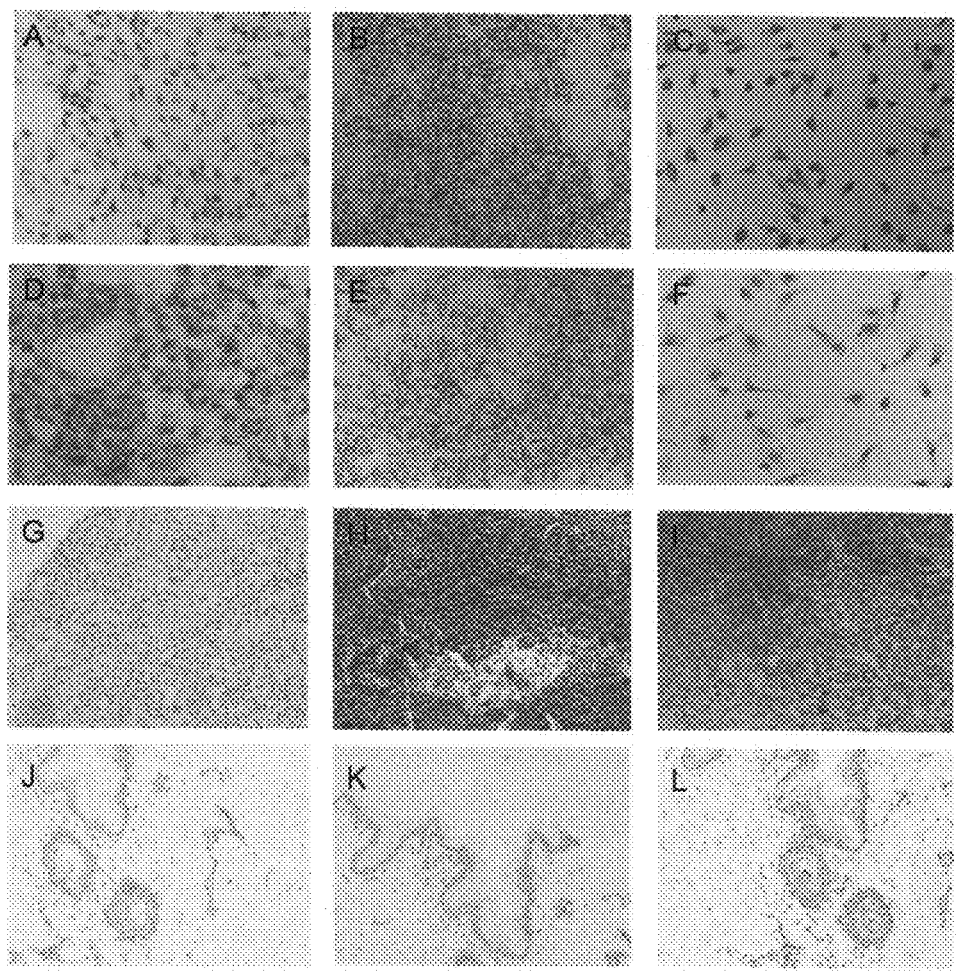

FIG. 4 Immuno-cytochemical and immuno-histochemical analysis of TUCAP-1.

Mice pre-immune serum immunocytochemical analysis of (A) MM2 cells; (B) peripheral blood lymphocytes; (C) in vitro differentiated macrophages.

TUCAP-1 immunocytochemical analysis of: (D) M2 cells; (E) peripheral blood cells; (F) Macrophages.

Immunohistochemical analysis of malignant melanoma tissues stained with: (G) preimmune mouse serum; (H) TUCAP-1 immune serum; and (1) anti-GP100.

Immunohistochemical analysis of healthy skin stained with: (J) mouse preimmune serum, (K) TUCAP-1 immune serum, and (L) anti-ezrin antibody. Magnification 10×.

Figure 5:
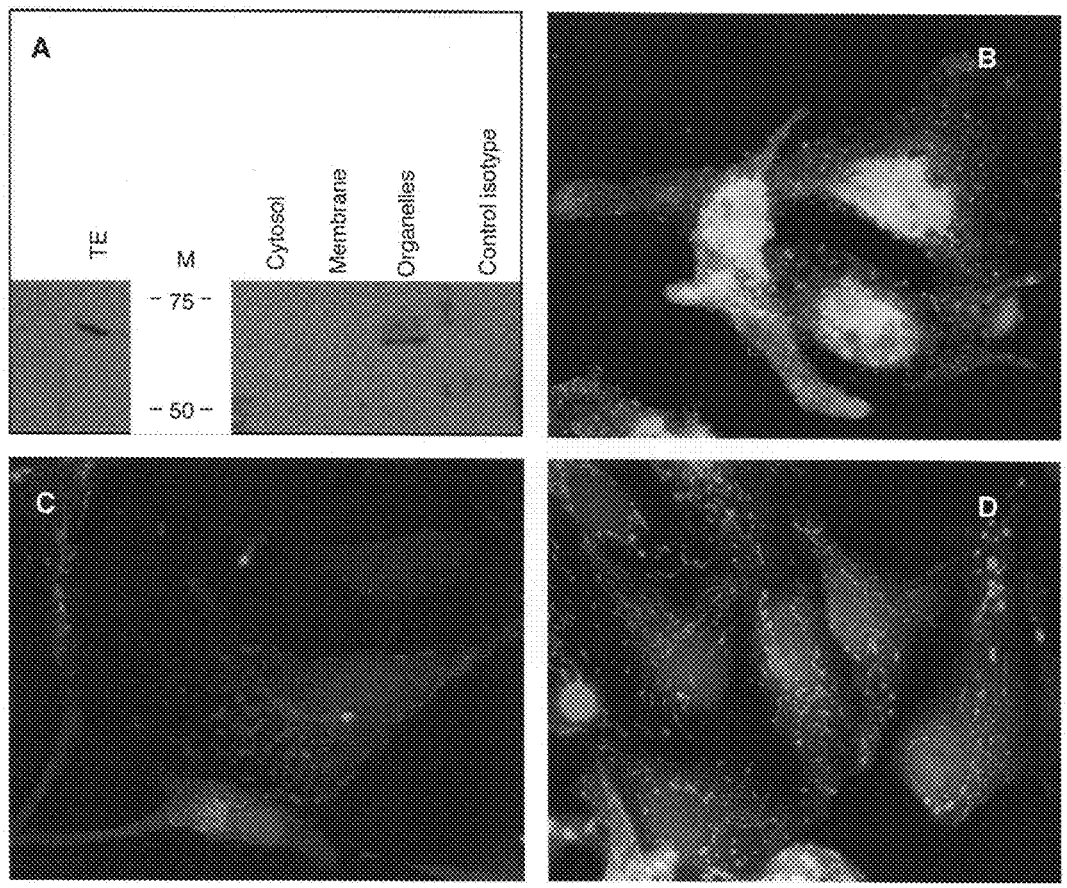

FIG. 5 Subcellular localization of TUCAP-1/-I (A) Western blot analysis of subcellular fractions of TUCAP-1 immunprecipitates from MM2 total lysates. M size marker, TE total extracts.

(B) Immunofluorescence (IF) double staining analysis of TUCAP-1 (green) and Rab5 (Red).

(C) IF double staining analysis of TUCAP-1 (green) and Lamp-1 (red).

(D) IF double staining analysis of TUCAP-1 (green) and Mitotracker stained mitochondria (red).

Yellow/orange areas indicate co-localization. Nuclei were stained with Hoechst 33258. Magnification 100×.

Figure 6:
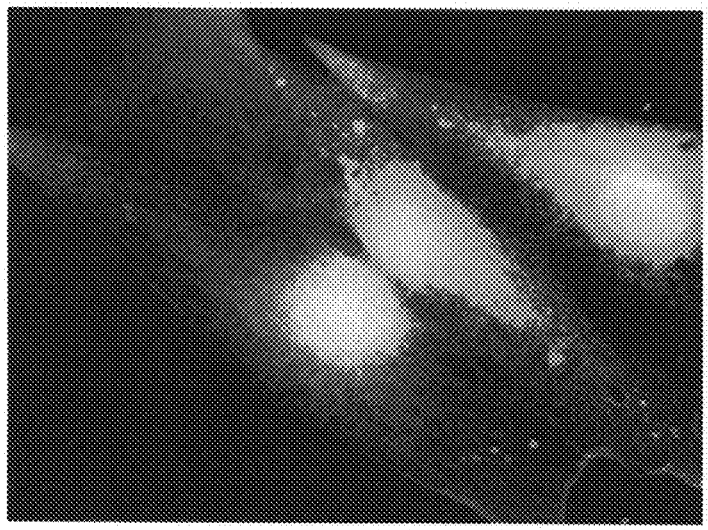

FIG. 6 Subcellular localization of TUCAP-1-II

Immunofluorescence (IF) double staining analysis of TUCAP-1 (green) and EEA1 (Red) on MM2 cells. Yellow/orange areas indicate co-localization. Nuclei were stained with Hoechst 33258. Magnification 100×.

Figure 7:
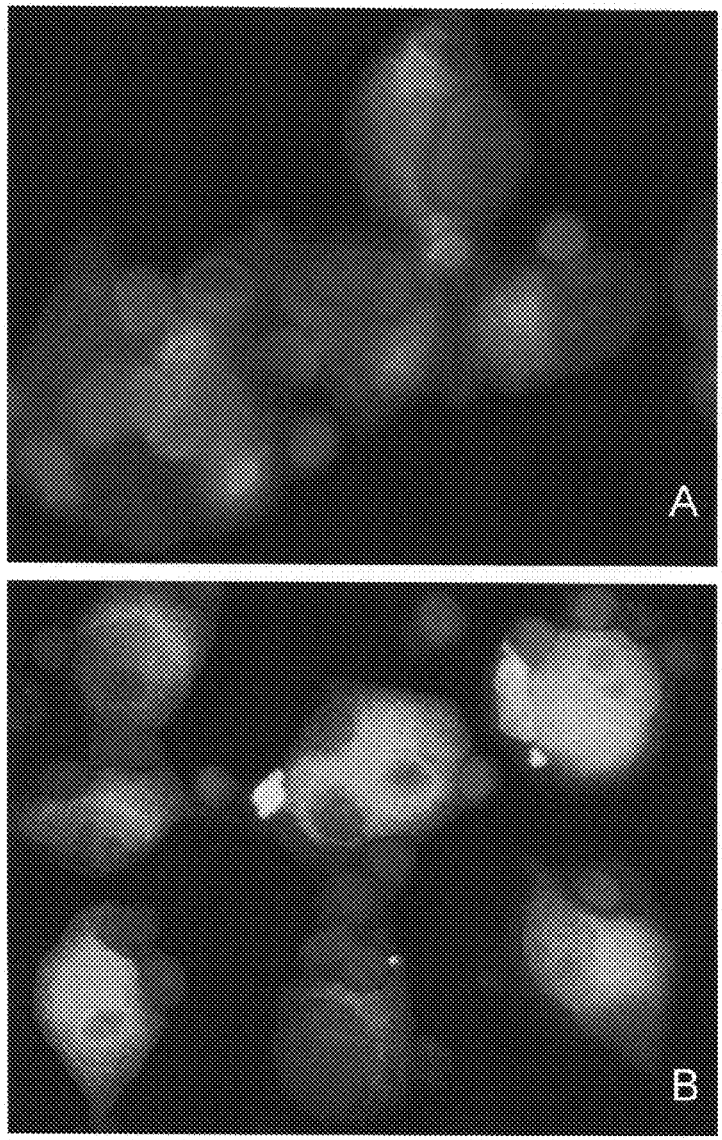

FIG. 7. TUCAP-1 detection in cannibal cells (A) Detection and localization of TUCAP-1 in metastatic melanoma MM1 cells co-cultured with living lymphocytes. IVM analysis of TUCAP-1 (green). Picture highlights that TUCAP-1 is detectable exclusively on melanoma cells.

(B) Double fluorescence analysis of TUCAP-1 (green) and EEA-1 (red) in metastatic melanoma MM1 cells co-cultured with living lymphocytes. Yellow/orange areas indicate co-localization. Nuclei are stained with Hoechst 33258.

Figure 8:
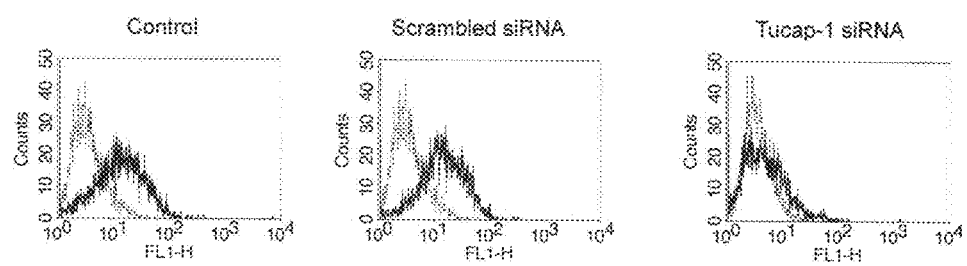

FIG. 8. FACS analysis of TUCAP-1 expression

Facs analysis of TUCAP-1 expression in untransfected MM2 cells, Scrambled siRNA and TUCAP-1 siRNA (TM9SF4 siRNA) transfected MM2 cells 48 hours after transfection.

Figure 9:
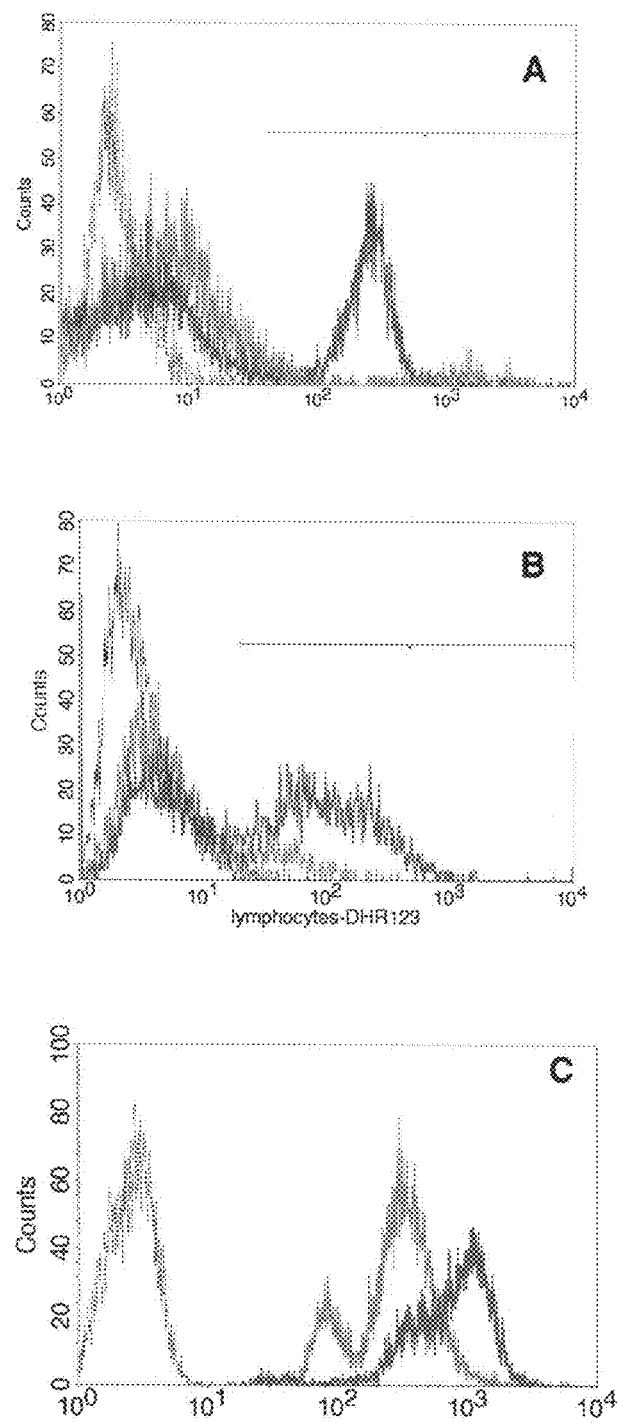

FIG. 9. Functional analysis of TM9SF4/TUCAP-1

(A), FACS analysis of phagocytic activity of Scrambled siRNA (SC-siRNA) or TUCAP-1 siRNA (TM9SF4 siRNA) transfected MM2 cells. Gray: unstained control cells; red: negative control Scrambled siRNA transfected cells; green: TM9SF4 siRNA transfected cells.

(B), FACS analysis of cannibal activity of SC-siRNA or TM9SF4 siRNA transfected MM2 cells incubated 18 hours with DHR123-stained lymphocytes. Gray: unstained control cells; red: SC-siRNA transfected cells; Green: TM9SF4 siRNA transfected. Cells. To exclude DHR123-stained lymphocytes not ingested with melanoma cells, exclusively melanoma cell fluorescence emission was evaluated.

(C) FACS analysis of LysoTracker DND-26 staining of SC-siRNA or TM9SF4 siRNA transfected MM2 cells. Gray: unstained control cells; red: SC-siRNA transfected; Green: TM9SF4 siRNA transfected.

Figure 10:
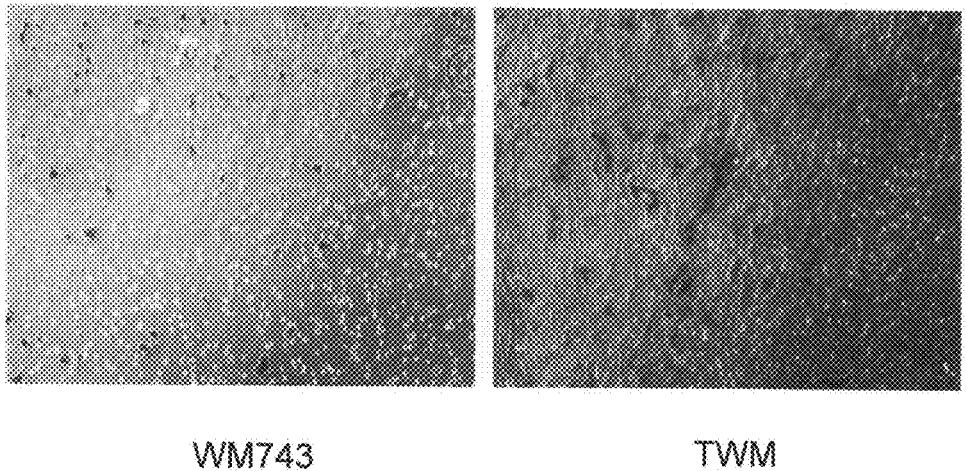

FIG. 10. TUCAP-1 overexpression enhance cell invasion through Matrigel. Phase micrograph of invading WM743 melanoma cells as compared to GFP-Tagged full length TUCAP-1 WM743 melanoma cells (TWM). Invading cells were Fixed in formaldehyde and stained with crystal violet. Picture clearly show that the number of invading cells was significantly higher for TWM, with a mean of 25 cells for untransfected versus a mean of 132 cells for TUCAP 1 transfected TWM.

DESCRIPTION OF THE INVENTION

TUCAP-1/TM9SF4 (HUGO nomenclature official committee official full name: transmembrane 9 superfamily protein member 4) belongs to the transmembrane 9 superfamily (TM9SF), a highly conserved family of proteins characterized by the presence of a large variable extracellular N-terminal domain and nine to ten putative transmembrane domains. However, function and localization of TM9SF4 has never been described in human cells. In this disclosure, we localize the protein expression and provide useful and novel applications to this protein. This disclosure identifies the protein as a novel oncoprotein and shows that the protein is expressed in malignant tumor cells while undetectable in variety of healthy cells and tissues. This disclosure also shows the structure of the protein and by analogy with other proteins shows that the protein may be involved in pH regulation of intracellular vesicles. Throughout this disclosure we call the protein TUCAP-1 and the gene coding for the protein is accordingly called tucap-1.

Table 1 below shows the physicochemical parameters of TUCAP-1 protein

| Tupac-1 ProtParam computation of physicochemical parameters: | |
| --- | --- |
| Number of amino acids: | 625 |
| Molecular weight: | 72541.3 |
| Theoretical pI: | 6.22 |
| Extinction coefficients: | 132880 |
| | Abs 0.1% (=1 g/l) 1.832, assuming ALL Cys residues appear as half cystines |
| | 132130 |
| | Abs 0.1% (=1 g/l) 1.821, assuming NO Cys residues appear as half cystines |
| Estimated half-life: | 30 hours (mammalian) |

Hydropathy analysis of TUCAP-1 through TopPred predictor server revealed a mostly hydrophilic, amino terminal portion that extends up to amino-acid 262, while the remaining portion of the protein is extremely hydrophobic and contains nine potential transmembrane domains (FIG. 1A) On the basis of this predicted structure it may be hypothesized with great confidence that TUCAP-1 is an integral membrane protein as shown in FIG. 1B Our finding that there is a fairly high homology between TUCAP-1 and PHG1 (45% that rises to 63% if NCBI Blast protein program positive alignment is considered) led us to a novel hypothesis that TUCAP-1 may have a role in cannibal activity of human metastatic melanoma cells.

According to one preferred embodiment of the present invention are polynucleotides corresponding or complementary to all or part of the tucap-1 gene, mRNAs, and/or coding sequences, preferably in isolated form, including polynucleotides encoding TUCAP-1 proteins and fragments thereof, DNA, RNA, DNA/RNA hybrid, and related molecules, oligonucleotides complementary to the tucap-1 gene or mRNA sequences or parts thereof, and polynucleotides or oligonucleotides which hybridize to the TUCAP-1 genes, mRNAs, or to TUCAP-1-encoding polynucleotides.

According to another preferred embodiment of the invention is an "antibody" which is a whole antibody molecule or fragment thereof that recognizes (or can bind to) "specific sequences" of TUCAP-1 protein, which is its antigen. Antibody may be either a polyclonal antibody or a monoclonal antibody. In this embodiment, TUCAP-1 protein is a polypeptide having the amino acid sequence according to SEQ ID NO: 1, and the specific sequences are polypeptides having an amino acid sequence containing deletion, substitution or addition of one or more amino acids as compared to the amino acid sequence of SEQ ID NO: 1 or a fragment of these. The antibody of the present invention encompasses antibody mutants. An "antibody mutant" is a mutant in which one or more amino acid residues in the antibody have been modified from the original.

According to further embodiments are TUCAP-1 inhibitors. Such inhibitor molecules may be polynucleotide sequences that are substantially complimentary to the sequence of SEQ ID NO: 2 or part of it, and oligonucleotide sequences substantially complimentary to a fragment of SEQ ID NO:2.

According to yet another embodiment of the invention are methods for treating cancer in a human patient comprising the step of administering to the patient a therapeutically effective amount of a composition comprising a TUCAP-1 binding agent conjugated to a chemotherapeutic drug. Antibodies and fragments that specifically bind to TUCAP-1 protein can be used to treat cancers. The invention includes the use of antibodies and antibody fragments that are fused to other moieties that can have a cytotoxic effect on cancer Another preferred embodiment of this invention is cell lines producing monoclonal antibodies against TUCAP-1 protein or fragments thereof.

According to yet another preferred embodiment are recombinant DNA or RNA molecules containing full-length wild type or mutated TUCAP-1 sequence, or deletion mutants of TUCAP-1, including but not limited to phages, plasmids, phagemids, cosmids, YACs, BACs, as well as various viral and non-viral expression vectors well known in the art, and cells transformed or transfected with such recombinant DNA or RNA molecules. Using these expression vectors, TUCAP-1 may be preferably expressed in several malignant tumor cell lines. Preferred embodiments comprise host-vector systems that are useful for the production of a TUCAP-1 protein or fragment thereof. Such host-vector systems may be employed: i) to study the functional properties of TUCAP-1 and TUCAP-1 mutations; ii) as model to develop a gene therapy protocol based on the utilization of TUCAP-1 silencing vectors and TUCAP-1 mutants expressing vectors.

Accordingly, this invention provides a unique tool to measure, study and detect TUCAP-1, as marker of malignancy of many cancer types. Moreover, this invention introduces a new tool for clinical oncologist in the management and follow up of cancer patients. Moreover, peptides of other molecules able to interfere the expression or acting as TUCAP-1 blocking agents are within the scope of this invention as antineoplastic compounds.

Yet another preferred embodiment of this invention is a kit to detect TUCAP-1 from tissue specimens and body fluids of tumor patients as a diagnostic and or prognostic tool such as a detection kit. Such kit comprises: a) anti TUCAP-1 antibodies; b) a positive control consisting of the purified TUCAP-1 protein, and the necessary buffers.

The invention is now described by means of examples, which are not meant to limit the scope of the invention. The scope of the invention is defined by the appended claims.

Example 1

Tucap-1 Transcripts and TUCAP-1 Protein are Detectable in Human Malignant Melanoma Cells, but not in Primary Melanoma Cells, in Peripheral Blood Mononuclear Cells or in Healthy Skin Cells Cell culture. Human primary and metastatic melanoma cell lines were respectively derived from primary or metastatic tumor lesions of patients surgically resected at the Istituto Nazionale dei Tumori, Milan, Italy. All cells employed in the current study were designated by PM (primary melanoma) or MM (metastatic melanoma), followed by a progressive number. Human peripheral blood mononuclear cells (PBMC) were purified by Ficoll-Hypaque (Pharmacia) density gradient of buffy coats from healthy donors. Monocytes were separated from PBMC by using CD14 labeled Miltenyi microbeads according to manufacturer's indications and were left to differentiate for 2 weeks at 37° C. in RPMI 1640 plus 15% FCS. Remaining peripheral blood lymphocytes (PBL), were obtained after CD14 beads mediated monocyte ablation. All the cells were seeded in RPMI 1640 supplemented with 100 IU/mL penicillin, 100 Ag/mL streptomycin, 10% FCS in a 5% CO2 environment at 37° C. (All reagents were purchased from Cambrex).

PCR analysis. Expression of Tucap-1 transcripts was assessed by rt-PCR on several primary and metastatic melanoma cell lines obtained from melanomas of patients surgically resected at Instituto Nazionale Tumori, Milan, as compared to peripheral blood lymphocytes (PBL). Total RNA from the cells was obtained by the RNAzol (Invitrogen) method and RNA templates were used for RT-PCR amplification. Primers for TUCAP-1 detection were:

```
tgtgtgaaacaagcgccttc,        (SEQ ID NO: 3
and atgaggtggacgtagtagt.         (SEQ ID NO: 4)
```

These primers amplify a fragment of 349 base pairs.

Primers used to direct TUCAP-1 His-tagged N-terminal domain synthesis were:

```
gaattcatgtgtgaaacaagcgcctt   (SEQ ID NO: 5)
and gtcgacagaaaaccagtggatctg.    (SEQ ID NO: 6)
```

Primers to detect GAPDH were:

```
ccatggagaaggctgggg           (SEQ ID NO: 7)
and caaagttgtcatggatgacc.        (SEQ ID NO: 8)
```

TUCAP 1 cloning and expression of TUCAP 1 fusion protein in human melanoma cells: PCR products were cloned into pTopo vector (Invitrogen) and then excised with the appropriate pair of restriction enzymes (EcoRI, SalI) to acquire a single fragment that was subsequently ligated in the pTrcHis2 vector (Invitrogen). The expressed recombinant protein was purified employing Ni NTA agarose resin (Qiagen) following manufacturer's instructions and utilized to immunize mice.

Primers that were used to direct GFP-tagged full length TUCAP-1 were:

```
gaattcatgtgtgaaacaagcg,      (SEQ ID NO: 9)
and gtcgatgtctatcttcacagcata.    (SEQ ID NO: 10)
```

PCR products were cloned into pTopo vector (Invitrogen) and then excised with the appropriate couple of restriction enzymes (EcoRI-SalI) and ligated to acquire a single fragment that subsequently was ligated in the pEGFPN1 vector (Clontech) at the EcoRI and SalI sites to produce the GFP-TUCAP-1 fusion protein. Plasmids encoding the GFP-TUCAP-1 fusion protein were transfected into MM1 and MM2 cells by using the Lipofectamine 2000 transfection kit (Invitrogen) according to the manufacturer's instructions, thus obtaining GFP-TUCAP-1 (GFP-Tuc) MM1 or MM2 cells. The percentage of transfected cells was evaluated by Fluorescence-activated cell sorting analysis.

Western Blotting and Immunoprecipitation

Bacterial lysates, whole melanoma cell lysates and CCD-1064SK healthy skin fibroblasts (SantaCruz) were resuspended in SDS sample buffer, denaturated by boiling, separated by SDS-PAGE, and analyzed by Western blot. 6xHis tagged protein, GFP, TUCAP-1, and GAPDH, were respectively detected with anti6His mAb (Sigma), anti GFP (clone 1E4 MBL), anti TUCAP-1 mouse serum and antiGAPDH (SantaCruz). TUCAP-1 proteins were immunoprecipitated overnight at 4° C. in the presence of protein A+G-Sepharose beads (Pierce) from precleared cell lysates, by using rabbit anti TUCAP-1 pAb antibody. Rabbit preimmune serum was used as negative control. Actin was detected with anti actin mAb (Sigma).

In order to characterize tucap-1 gene product, cDNA derived from MM1 cells was cloned in bacterial expression vectors to obtain TUCAP-1 first 265 amino acids fused to a 6-Histidine N-terminal tag (6H-Nt-TUCAP 1) (SEQ ID NO:11) Western blot analysis of purified recombinant protein resulted in a translation product of about 30 kDa absent in control bacterial whole lysates (negative control). Therefore, His-tagged TUCAP-1 recombinant peptide was employed as immunogen to produce anti-TUCAP-1 antibodies in mice. The specificity of the TUCAP-1 antiserum was determined by Western blot analysis of the purified 6H-Nt-TUCAP-1 immunoblotted with anti 6His and TUCAP-1 mouse antisera (FIG. 2B). TUCAP-1 mouse antiserum was further analyzed by Western blot on Triton soluble and Triton insoluble fractions of MM1 cells transfected or not transfected with a GFP-tagged full length TUCAP-1 (GFP-TUCAP-1). The anti-GFP antibody revealed a single specific translation product in the 100 kDa range, while anti-TUCAP-1 antibodies recognized both the GFP-tagged and the endogenous TUCAP-1 corresponding to a 70 kDa protein detectable in both cell lines (FIG. 2C). Interestingly, TUCAP-1 was more represented in the Triton insoluble fractions (GAPDH negative, cytoskeletal proteins enriched fraction), thus supporting the provisional models proposing TUCAP-1 as a transmembrane protein. To further support PCR results, the anti-TUCAP-1 antibodies were blotted in cellular extracts of four metastatic melanoma cells (MM2-MM5), previously analyzed for their cannibal behavior as compared to healthy skin fibroblasts (HSC) and GFP-TUCAP-1 transfected MM2 cells, as a control. TUCAP-1 was exclusively detectable in melanoma cells, while undetectable in skin cells (FIG. 3).

Example 2

Immunochemistry shows TUCAP-1 exclusively in melanoma cells Immunocytochemistry and immunohistochemistry. For immunocytochemistry melanoma cells and macrophages, cultured on glass chamber slides (Falcon), and PBL, cytospun on glass slides, were fixed with 80% methanol 10 minutes at 4° C. and stained for TUCAP-1, TUCAP-1 mouse serum or preimmune control serum. Malignant melanoma and corresponding normal skin tissue from Biomax array slides (Biomax) were immunostained with pre-immune serum, for anti-TUCAP-1 mouse antiserum. Melanoma was also stained for anti-gp100 (Immunotech) while normal skin was also stained for anti-ezrin (Sigma). Proteins were visualized using the peroxidase antiperoxidase method in single staining (Dako) and counterstained with Mayer's hematoxylin.

FIG. 4A-C shows that MM2 cell lines (A), Peripheral blood lymphocytes (B), and in vitro differentiated Macrophages (C), were negative for mouse preimmune serum. Consistently with PCR results malignant melanoma cultured cells showed clear positive staining for TUCAP-1 (FIG. 4 D) while PBL (FIG. 4E) and macrophages (FIG. 4F) were negative for TUCAP1 staining. Immunohistochemical analysis of malignant melanoma tissues as compared to healthy skin suggested that TUCAP-1 was detectable only in melanoma tissues (FIG. 4H) while undetectable in healthy skin (4K). As positive control markers for melanoma and normal skin GP100 (FIG. 4I), and ezrin (FIG. 4L) were used respectively. Pre-immune mouse serum staining was always negative in both tissues (FIG. 4G, 4J). These results provide clear evidence that TUCAP-1 was exclusively detectable in melanoma cells and thus support the results of Example 1.

Example 3

Subcellular Localization of TUCAP-1

Further experiments were performed to analyze the intracellular localization of TUCAP 1.

Cell compartment fractionation Cells were harvested and processed according to Qproteome plasma membrane kit protocol (Quiagen) in order to obtain non denatured fractions of cellular compartments corresponding to purified plasma membranes and cytosol. The latter fractions were then precipitated with acetone and resuspended in immunoprecipitation buffer B (0.1% SDS, 1% NP40, 0.5% sodium cholate) in order to be subjected to immunoprecipitation with rabbit anti TUCAP-1. Residual pellet from cellular compartment fractionation, containing intact cells and organelles, was deprived of the former through centrifugation and subjected to Triton X-100 extraction in order to obtain soluble and insoluble fractions which were immunoprecipitated with rabbit anti TUCAP-1. Following electrophoresis of samples, the nitrocellulose was blotted with mouse anti-TUCAP-1.

Immunofluorescence analyses MM2 cells were seeded on cover glass placed in 60-mm Petri dishes. Cells were fixed with 2% paraformaldehyde and permeabilized (Triton X-100 (0.1%) or 24 hours. For TUCAP 1 and Rab5 double staining cells were labeled with mouse anti-TUCAP-1 serum and rabbit anti-Rab5 (SantaCruz) and respectively revealed with Alexa Fluor 488-conjugated anti-mouse IgG and anti-rabbit Alexa Fluor 594-conjugated IgG (Molecular Probes). For TUCAP-1 and Lamp-1 detection cells were labeled with rabbit anti-TUCAP-1 pAb and mouse anti Lamp-1 Mab, (BD Pharmingen) respectively, stained with Alexa Fluor 594-conjugated anti-rabbit IgG and Alexa Fluor 488-conjugated anti-mouse IgG. TUCAP-1 and mitochondria were detected by staining TUCAP-1 with anti-TUCAP-1 mouse pAb and labeled with Alexa Fluor 488-conjugated anti-mouse IgG, while mitochondria were labeled with Mithotracker Red (Invitrogen). After washings, all samples were mounted with glycerol:PBS (2:1) and observed with a Leica DM 2500 fluorescence microscope. Images were recorded with a Spot Insight digital camera (Delta Sistemi) equipped with IAS 8.2 system of image analysis (Delta Sistemi).

MM2 whole cell lysates were immunoprecipitated with anti-TUCAP-1 antibodies and various subcellular fractions were separated and analyzed by Western blot. The results revealed that TUCAP-1 was mainly recovered in fractions enriched for cellular organelles, while undetectable in sytosolic and plasma membrane fractions (FIG. 5A). In order to identify subcellular localization of TUCAP-1, MM2 cells were double stained for TUCAP-1, and either for the early endosomal markers Rab5, or for the component of late endosomes and lysosomes Lamp-1, or the mitochondrial marker Mitotracker™. Fluorescence microscopy analysis showed that TUCAP-1 co localized with both Rab5 (FIG. 5B) and EEA-1 (FIG. 6 and FIG. 7B), while it did not co-localize with either Lamp-1 (FIG. 5C), Mitotracker™ (FIG. 5D) or Hoechst stained nuclei.

Moreover, FIG. 7 shows the double staining fluorescence on same cells co-cultured with living lymphocytes. TUCAP-1 is detectable exclusively on the surface of melanoma cells, while lymphocytes are completely unstained (FIG. 7A). Again, TUCAP-1 co-localizes with the primary endosome marker EEA-1 (FIG. 7B) confirming the expression of this protein on early endosomes.

Example 4

Functional Analysis of TUCAP-1

Tucap-1 Silencing Inhibits Phagocytic Behaviour

The role of TUCAP-1 protein in human metastatic melanoma cells was evaluated by inhibiting its expression trough Tucap-1 silencing.

The following StealthR RNAi duplexes (Invitrogen) were used for tucap-1 silencing:

```
gagugacguccagauccacugguuu,    (SEQ ID NO: 13)
and aaaccaguggaucuggacgucacuc,    (SEQ ID NO: 14)
``` and annealed according to the manufacturer's instructions. As a negative control Stealth RNAi Negative control medium GC duplexes (Invitrogen) was used. Melanoma cells were transfected using Lipofectamine RNAiMAX reagent (Invitrogen) according to the manufacturer's instructions. Briefly the day before transfection, melanoma cells were seeded in six-well plates (1×10$^5$ per well), and after 24 hours, cells were transfected with 30 pmol of siRNA per well. 48 hours after transfection, cells were analyzed for TUCAP-1 expression by FACS analysis.

Three different phagocytic metastatic cell lines were transfected with small interfering RNA to Tucap-1 (Tucap-1 siRNA), or transfected with an unrelevant siRNA oligo (SC-siRNA). FIG. 8 shows FACS analysis of TUCAP-1 expression on untransfected MM2 cells and Scrambled siRNA or TUCAP-1 siRNA transfected MM2 cells 48 hours after transfection. Similar results were obtained in scrambled and TUCAP-1 silenced MM3 cells (not shown). This confirmed an effective knockdown of TUCAP-1.

To assess the phagocytic activity of these cells, we first measured the ability of untransfected, SC-siRNA transfected, or Tucap-1 silenced melanoma cell lines to ingest stained yeast cells or living lymphocytes. 48 hours after transfection, SC-siRNA or TUCAP-1 siRNA transfected MM2 and MM3 melanoma cells were incubated at 37° C. with FITC stained *Saccaromyces* yeasts FITC (1:60), or 10 uMol dihydrorhodamine 123 (DHR123) (Molecular Probes) stained living lymphocytes (1:10). Phagocytosis/cannibalism was measured after 4 hours by washing away the excess lymphocytes or yeast cells with PBS and adding a PBS solution containing trypisn (1.5 g/L) EDTA (0.44 g/L). After washings, melanoma cells were harvested and analyzed on a cytometer equipped with a 488-nm argon laser. At least 10,000 venets were acquired and analyzed by a Macintosh computer using CellQuest software (Becton Dickinson). Melanoma cells that appeared fluorescent in green were considered as phagocytic/cannibal. The results showed that the TUCAP-1 knocking-down markedly inhibited both the phagocytic and the cannibal activity of melanoma cells (FIG. 9A, 9B, Table 1), proving that TUCAP-1 plays a key role in the cannibal behavior of metastatic human melanomas and the protein thus can be used as a marker of malignancy.

TABLE 2

Role of TUCAP-1 in phagocytosis/cannibalism
Phagocytic/Cannibal activity of scrambled siRNA transfected (SC-siRNA) and Tucap-1 silenced (Tucap-1 siRNA) MM2 and MM3 metastatic melanoma cells against FITC stained yeasts and DHR123 stained live lymphocytes. The phagocytic activity was expressed as % of phagocytic cells. Numbers are mean ± s.d. of 5 different experiments.

| | Yeasts | | Live lymphocytes | |
|---|---|---|---|---|
| | SC-siRNA | Tucap-1 siRNA | SC-siRNA | Tucap-1 siRNA |
| MM2 | 37 ± 1 | 4 ± 2 | 45 ± 5 | 17 ± 9 |
| MM3 | 43 ± 14 | 14 ± 12 | 40 ± 9 | 9 ± 7 |

Example 5

TUCAP-1 has a Role in Regulating Acidification of Endosomal Vesicles

Scrambled siRNA transfected and TUCAP-1 silenced MM2 and MM3 cells were stained with 1 μM LysoTracker probe (Molecular Probes) for 30 minutes at 37° C. and immediately analyzed by a cytometer. Comparisons among different melanoma cell lines were conducted by CellQuest software using the median values of fluorescence intensity histograms.

Based on the result that TUCAP-1 localizes on Rab5 bearing endosomes (see EXAMPLE 3), we tested a hypothesis that TUCAP-1 protein may have a role in the pH regulation of phago/endosomal compartments of malignant tumor cells. To verify this hypothesis, control SC-RNAi and TUCAP-1-siRNA transfected cells were stained with the acidotropic probe LysoTracker green and analyzed by flow symmetry. Tucap-1 gene silencing induced appearance of less acidic vesicle within melanoma cells, as compared to SC-RNA transfected control cells (FIG. 9C). These experiments support the hypothesis that TUCAP-1 has a role in regulating acidification of internal vesicles, such as early endosomes.

Example 6

TUCAP-1 Involvement in Early Phases of Metastatic Process

Ongoing experiments based on using TUCAP-1 overexpressing cells suggest that this protein is involved in tumor cell invasiveness during early phases of metastatic process. Cell invasion capability of these cells is assayed by using Matrigel invasion chambers (Becton-Dickenson, Bedford, Mass., USA). Briefly, untransfected WM743 or GFP-Tagged full length TUCAP-1 WM743 melanoma cells (TWM) were resuspended in serum free medium and loaded into the top chamber, while in the bottom chamber was placed in medium added with 10% FCS as a chemoattractant. Cells were incubated at 37° C. in a humidified atmosphere and allowed to migrate through the chemotaxis chamber for 48 hours. After incubation, the cells remaining at the upper surface were completely removed using a cotton carrier. The migrated cells on the bottom of chemotaxis chamber were stained with crystal violet. Invading cells were counted microscopically (40×) in four different fields per filter. FIG. 10 shows the lower side of transwell membrane, clearly indicating that the number of invading cells was significantly higher for TWM, with a mean of 25 cells for untransfected versus a mean of 132 cells for TUCAP 1 transfected TWM cells.

Example 7

TUCAP-1 Involvement in Cisplatin Resistance of Melanoma Cells

Several publications show the role of proteins involved in ion trafficking and the role of endo-lysosmal compartment in drug sequestering, inactivation and extrusion as mechanisms of drug resistance. TUCAP 1 expression in early endosomes and its involvement in pH regulation of endosomal vesicles (as shown in above examples) led us to hypothesize a role for this protein in drug resistance of cancer cell. To prove this, MM2 melanoma cells, highly expressing TUCAP-1, were pretreated with Scrambled (SC-siRNA) or Tucap-1 si-RNA for 48 hours (as shown in the previous examples), and after transfection cells were treated with 2 uM cisplatin. 48 hours after cisplatin induced cytotoxicity was evaluated by FACS analysis of early (annexin-V single positive) and late (PI/Annexin V double positive) apoptosis. Tucap-1 silencing markedly increased cytotoxic effects of cisplatin as compared to Scrambled-si-RNA treated WM743 cells that behaved as the untransfected control cells. With a mean of 63% of live cells in control transfected cells versus a mean of 37% in TUCAP-1 silenced cells.

This set of experiments proves that TUCAP-1 is involved in drug resistance of TUCAP-1 over expressing cells and that tucap-1 silencing is a promising method to inhibit phagocytotic character of tumor cells.

Based on the results shown in above examples, the present disclosure also provides highly sensitive and specific methods for detection of melanoma and several other tumors characterized by a described phagocytic behaviour i.e. breast cancer, lung carcinoma, bladder cancer, medulloblastoma, and gastric adenocarcinoma. Moreover, this disclosure provides means to distinguish malignant from benign cancer lesions by showing that TUCAP-1 is exclusively expressed in malignant tumors. Methods for cancer detection comprise evaluation of a biological sample from a putative cancer lesion, typically by in situ hybridization, rt-PC, or immunoenzymatic methods.

Example 8

Polyclonal and Monoclonal Antibodies to TUCAP-1

Based on the examples above, polyclonal (pAb) and monoclonal antibodies (mAb) specific for TUCAP-1 would be useful for various purposes, including for example diagnostics to determine malignancy of a tumor, and treatment of cancer.

In order to produce polyclonal antibodies, cDNA from MM1 cells was cloned in bacterial expression vectors to obtain TUCAP-1 aminoacids 18-282 fused to a 6-Histidine N-terminal tag (SEQ ID NO:11). Purified recombinant peptide was used to produce anti-TUCAP-1 antibodies in mice. The anti-TUCAP-1 antibodies recognized immunogen, GFP-tagged full length protein as positive control as well as endogenous TUCAP-1 protein.

Polyclonal antibodies were also generated by immunizing rabbit, goat and donkey with a purified peptide fragment having an amino acid sequence according to SEQ ID NO: 12. The antibodies generated were able to recognize human TUCAP-1 protein by binding to a peptide fragment that consists of amino acids 221-235 of SEQ ID NO: 1. Polyclonal antibodies are also obtained by immunizing goat and donkey.

In order to produce monoclonal antibodies, mice were immunized with a peptide fragment having amino acid sequence according to SEQ ID NO:11 or SEQ ID NO:12 or a fragment thereof. Alternatively mice are immunized with peptide fragment having amino acid sequence according to SEQ ID NO: 15. Selected hybridoma clones were generated by using spleen cells of selected mice. Briefly B-cells deriving from spleen of immunized mice were fused with a myeloma tumor cell line specifically selected for hybridoma production. The deriving fused (hybrid) cells that can grow indefinitely in culture with consequent production large amounts of the desired antibodies. Hybridoma production was performed according to standard protocols. After screening the selected hybridomas, the hybridomas are cloned and grown to large-scale for antibody production. Various positive hybridomas are selected for different uses, for example: a) laboratory experimental uses (Western Blot, immuno-precipitation, FACS analysis, immunofluorescence and immunohisto- and immunocyto-chemical analysis of human tissues and cultured cells); b) preclinical and clinical studies, c) tumor diagnosis and prognosis tools, such as detection kit. The monoclonal antibodies produced bind to conformational or linear epitopes of TUCAP-1 protein amino acids 18-282 of SEQ ID NO: 1 or peptide fragment consisting of amino acids 221-235 or consisting of aminoacids 303-352 of SEQ ID NO: 1. The antibodies also bind to TUCAP-1 protein of mouse, rat, cat, dog, and sheep origin.

The examples above disclose particular embodiments of the invention in detail. However, this has been done by way of example and for the purposes of illustration only. The examples are not intended to limit the scope of the appended claims, which define the invention.

REFERENCES

Bukrinskaya A, Brichacek B, Mann A, Stevenson M. Establishment of a functional human immunodeficiency virus type 1 (HIV-1) reverse transcription complex involves the cytoskeleton. J Exp Med. 1998; 188:2113-2125.

Caruso R A, Muda A O, Bersiga A, Rigoli L, Inferrera C. Morphological evidence of neutrophil-tumor cell phagocytosis (cannibalism) in human gastric adenocarcinomas. Ultrastruct Pathol 2002; 26:315-21.

Chou, K. C. (2005). "Using amphiphilic pseudo amino acid composition to predict enzyme subfamily classes". Bioinformatics, 21, 10-19.

DeSimone P A, East R, Powell R D. Phagocytic tumor cell activity in oat cell carcinoma of the 6y7y-j - - - ol 1980; 11:535-9.

Fujii M, Ishii Y, Wakabayashi T, et al. Cytologic diagnosis of male breast cancer with nipple discharge. A case report. Acta Cytol 1986; 30:2

Gasteiger E., Gattiker A., Hoogland C., Ivanyi I., Appel R. D., Bairoch A. ExPASy: the proteomics server for in-depth protein knowledge and analysis Nucleic Acids Res. 31:3784-3788(2003).

Kojima S, Sekine H, Fukui I, Ohshima H. Clinical significance of "cannibalism" in urinary cytology of bladder cancer. Acta Cytol 1998; 42:1365-9.

Kumar P V, Hosseinzadeh M, Bedayat G R. Cytologic findings of medulloblastoma in crush smears. Acta Cytol 2001; 45:542-6.

Lugini L, Lozupone F, Matarrese P, Funaro C, Luciani F, Malorni W, Rivoltini L, Castelli C, Tinari A, Piris A, Parmiani G, Fais S. Potent phagocytic activity discriminates metastatic and primary human malignant melanomas: a key role of ezrin. Lab Invest. 2003 November; 83(11): 1555-67.

Lugini L, Matarrese P, Tinari A, Lozupone F, Federici C, Iessi E, Gentile M, Luciani F, Parmiani G, Rivoltini L, Malorni W, Fais S. Cannibalism of live lymphocytes by human metastatic but not primary melanoma cells. Cancer Res. Apr. 1, 2006; 66(7):3629-38.

B Rost, G Yachdav and J Liu (2004) Server. Nucleic Acids Research 32 (Web Server issue): W321-W326

B Rost (1996) Methods in Enzymology, 266:525-539

Shen, H. B. and Chou, K. C (2007) "Hum-mPLoc: an ensemble classifier for large-scale human protein subcellular location prediction by incorporating samples with multiple sites", Biochemical and Biophysical Research Communications. 355(4): 1006-11.

Sloane B F, Dunn J R, Honn K V. Lysosomal cathepsin B: correlation with metastatic potential. Science 1981; 212: 1151-3.

Steinhaus J. Ueber carcinoma-einschlusse. Virchows Arch 1891; 126:533-5.

Stroebe H. Zur Kenntniss verschiedener cellularer Vorgange und Erscheinungen in Geschwulsten. Beitrage Pathol 1892; 11:1.

Shen, H. B. and Chou, K. C. (2006). "Ensemble classifier for protein folding pattern recognition". Bioinformatics, July 15; 22(14):1717-22.

What is claimed is:

1. A method to distinguish metastatic tumors from non-metastatic tumors, said method comprising a step of determining presence or absence of expression of SEQ ID NO: 1 in tumor cell, wherein presence of the expression indicates metastatic character of the cell.

2. The method of claim 1, wherein the presence or absence of expression of SEQ ID NO:1 is determined by using RT-PCR, immunoenzymatic method or in situ hybridization.

3. The method of claim 1, wherein presence or absence of amino acid sequence selected from the group consisting of SEQ ID NO: 11, SEQ ID NO: 12 and SEQ ID NO: 15 is determined.

4. A method to follow up development of metastatic activity of a tumor, said method comprising a step of determining presence or absence of expression of SEQ ID NO: 1 in tumor cell, wherein presence of the expression indicates metastatic character of the cell.

5. The method of claim 4, wherein presence of absence of amino acid sequence selected from the group consisting of SEQ ID NO: 11, SEQ ID NO: 12 and SEQ ID NO:15 is determined.

6. The method of claim 4, wherein the tumor is melanoma tumor.

7. A method to detect presence of metastatic tumors in vitro, said method comprising the steps of:
   a) providing a kit comprising antibodies capable of recognizing human TUCAP-1 protein by binding to a peptide fragment selected from the groups consisting of amino acid 18-282, 221-235 and 303-352 of SEQ ID NO:1 and a titered positive control comprising a peptide fragment having an amino acid sequence selected from the group consisting of SEQ ID NO:1, SEQ ID NO:11, SEQ ID NO:12 and SEQ ID NO:15; and b) allowing the antibodies recognize TUCAP-protein from tissues and body fluids of patients with tumors, wherein antibody recognizing TUCAP-protein indicates presence of metastatic tumor character.

8. The method of claim 7, wherein the tumor is melanoma tumor.

9. A method to detect phagocytic metastatic cells by determining presence or absence of expression of SEQ ID NO: 1 in the cells, wherein the presence of the expression indicates presence of phagocytic metastatic cells.

* * * * *

SEQUENCE LISTING

<160> NUMBER OF SEQ ID NOS: 15

<210> SEQ ID NO 1
<211> LENGTH: 642
<212> TYPE: PRT
<213> ORGANISM: Homo sapiens

<400> SEQUENCE: 1

```
Met Ala Thr Ala Met Asp Trp Leu Pro Trp Ser Leu Leu Leu Phe Ser
1               5                   10                  15

Leu Met Cys Glu Thr Ser Ala Phe Tyr Val Pro Gly Val Ala Pro Ile
            20                  25                  30

Asn Phe His Gln Asn Asp Pro Val Glu Ile Lys Ala Val Lys Leu Thr
        35                  40                  45

Ser Ser Arg Thr Gln Leu Pro Tyr Glu Tyr Tyr Ser Leu Pro Phe Cys
    50                  55                  60

Gln Pro Ser Lys Ile Thr Tyr Lys Ala Glu Asn Leu Gly Glu Val Leu
65                  70                  75                  80

Arg Gly Asp Arg Ile Val Asn Thr Pro Phe Gln Val Leu Met Asn Ser
                85                  90                  95

Glu Lys Lys Cys Glu Val Leu Cys Ser Gln Ser Asn Lys Pro Val Thr
            100                 105                 110

Leu Thr Val Glu Gln Ser Arg Leu Val Ala Glu Arg Ile Thr Glu Asp
        115                 120                 125

Tyr Tyr Val His Leu Ile Ala Asp Asn Leu Pro Val Ala Thr Arg Leu
    130                 135                 140

Glu Leu Tyr Ser Asn Arg Asp Ser Asp Asp Lys Lys Lys Glu Lys Asp
145                 150                 155                 160

Val Gln Phe Glu His Gly Tyr Arg Leu Gly Phe Thr Asp Val Asn Lys
                165                 170                 175

Ile Tyr Leu His Asn His Leu Ser Phe Ile Leu Tyr Tyr His Arg Glu
            180                 185                 190

Asp Met Glu Glu Asp Gln Glu His Thr Tyr Arg Val Val Arg Phe Glu
        195                 200                 205

Val Ile Pro Gln Ser Ile Arg Leu Glu Asp Leu Lys Ala Asp Glu Lys
    210                 215                 220

Ser Ser Cys Thr Leu Pro Glu Gly Thr Asn Ser Ser Pro Gln Glu Ile
225                 230                 235                 240

Asp Pro Thr Lys Glu Asn Gln Leu Tyr Phe Thr Tyr Ser Val His Trp
                245                 250                 255

Glu Glu Ser Asp Ile Lys Trp Ala Ser Arg Trp Asp Thr Tyr Leu Thr
            260                 265                 270

Met Ser Asp Val Gln Ile His Trp Phe Ser Ile Ile Asn Ser Val Val
        275                 280                 285

Val Val Phe Phe Leu Ser Gly Ile Leu Ser Met Ile Ile Arg Thr
    290                 295                 300

Leu Arg Lys Asp Ile Ala Asn Tyr Asn Lys Glu Asp Asp Ile Glu Asp
305                 310                 315                 320

Thr Met Glu Glu Ser Gly Trp Lys Leu Val His Gly Asp Val Phe Arg
                325                 330                 335

Pro Pro Gln Tyr Pro Met Ile Leu Ser Ser Leu Leu Gly Ser Gly Ile
            340                 345                 350

Gln Leu Phe Cys Met Ile Leu Ile Val Ile Phe Val Ala Met Leu Gly
        355                 360                 365
```

```
Met Leu Ser Pro Ser Ser Arg Gly Ala Leu Met Thr Thr Ala Cys Phe
    370                 375                 380

Leu Phe Met Phe Met Gly Val Phe Gly Phe Ser Ala Gly Arg Leu
385                 390                 395                 400

Tyr Arg Thr Leu Lys Gly His Arg Trp Lys Lys Gly Ala Phe Cys Thr
                405                 410                 415

Ala Thr Leu Tyr Pro Gly Val Val Phe Gly Ile Cys Phe Val Leu Asn
            420                 425                 430

Cys Phe Ile Trp Gly Lys His Ser Ser Gly Ala Val Pro Phe Pro Thr
        435                 440                 445

Met Val Ala Leu Leu Cys Met Trp Phe Gly Ile Ser Leu Pro Leu Val
    450                 455                 460

Tyr Leu Gly Tyr Tyr Phe Gly Phe Arg Lys Gln Pro Tyr Asp Asn Pro
465                 470                 475                 480

Val Arg Thr Asn Gln Ile Pro Arg Gln Ile Pro Glu Gln Arg Trp Tyr
                485                 490                 495

Met Asn Arg Phe Val Gly Ile Leu Met Ala Gly Ile Leu Pro Phe Gly
            500                 505                 510

Ala Met Phe Ile Glu Leu Phe Phe Ile Phe Ser Ala Ile Trp Glu Asn
        515                 520                 525

Gln Phe Tyr Tyr Leu Phe Gly Phe Leu Phe Leu Val Phe Ile Ile Leu
    530                 535                 540

Val Val Ser Cys Ser Gln Ile Ser Ile Val Met Val Tyr Phe Gln Leu
545                 550                 555                 560

Cys Ala Glu Asp Tyr Arg Trp Trp Trp Arg Asn Phe Leu Val Ser Gly
                565                 570                 575

Gly Ser Ala Phe Tyr Val Leu Val Tyr Ala Ile Phe Tyr Phe Val Asn
            580                 585                 590

Lys Leu Asp Ile Val Glu Phe Ile Pro Ser Leu Leu Tyr Phe Gly Tyr
        595                 600                 605

Thr Ala Leu Met Val Leu Ser Phe Trp Leu Leu Thr Gly Thr Ile Gly
    610                 615                 620

Phe Tyr Ala Ala Tyr Met Phe Val Arg Lys Ile Tyr Ala Ala Val Lys
625                 630                 635                 640

Ile Asp

<210> SEQ ID NO 2
<211> LENGTH: 4028
<212> TYPE: DNA
<213> ORGANISM: Homo sapiens

<400> SEQUENCE: 2
ccaagatggc gacggcgatg gtgagtgaag gagactccgg gagcgggagc tggagcgggg    60
ccctccgggg tatcccagga tcttccagca ccccatgcct ggccctgagc cacctccggg   120 accccctgact caggcctgag ggctacctct gactgggctt gtcttccccg aaatccacct   180
ccctggccct gccctgcac tcaggcttgt gaaggcccg agttttgggg gaggcgccgt     240
ttcggaggaa gacctcggct gctgccttcg ccggttccca ttctactttt ggtctccgcc   300
cactgattgg ttgccgtggt ctttactgct tttctccctg atgtgtgaaa caagcgcctt   360
ctatgtgcct ggggtcgcgc ctatcaactt ccaccagaac gatcccgtag aaatcaaggc   420
tgtgaagctc accagctctc gaacccagct accttatgaa tactattcac tgcccttctg   480
ccagcccagc aagataaccct acaaggcaga gaatctggga gaggtgctga gggggaccg   540
```

-continued

```
gattgtcaac accccttcc aggttctcat gaacagcgag aagaagtgtg aagttctgtg   600
cagccagtcc aacaagccag tgaccctgac agtggagcag agccgactcg tggccgagcg   660
gatcacagaa gactactacg tccacctcat tgctgacaac ctgcctgtgg ccacccggct   720
ggagctctac tccaaccgag acagcgatga acaagaagaa gaaaaagatg tgcagtttga   780
acacggctac cggctcggct tcacagatgt caacaagatc tacctgcaca accacctctc   840
attcatcctt tactatcatc gggaggacat ggaagaggac caggagcaca cgtaccgtgt   900
cgtccgcttc gaggtgattc cccagagcat caggctggag gaccctcaaag cagatgagaa   960
gagttcgtgc actctgcctg agggtaccaa ctcctcgccc caagaaattg accccaccaa  1020
ggagaatcag ctgtacttca cctactctgt ccactgggag gaaagtgata tcaaatgggc  1080
ctctcgctgg gacacttacc tgaccatgag tgacgtccag atccactggt tttctatcat  1140
taactccgtt gttgtggtct tcttcctgtc aggtatcctg agcatgatta tcattcggac  1200
cctccggaag gacattgcca actacaacaa ggaggatgac attgaagaca ccatggagga  1260
gtctgggtgg aagttggtgc acggcgacgt cttcaggccc cccagtaccc ccatgatcct  1320
cagctccctg ctgggctcag gcattcagct gttctgtatg atcctcatcg tcatctttgt  1380
agccatgctt gggatgctgt cgccctccag ccggggagct ctcatgacca cagcctgctt  1440
cctcttcatg ttcatggggg tgtttggcgg attttctgct ggccgtctgt accgcacttt  1500
aaaaggccat cggtggaaga aggagccttt ctgtacggca actctgtacc ctggtgtggt  1560
ttttggcatc tgcttcgtat tgaattgctt catttgggga aagcactcat caggagcggt  1620
gccctttccc accatggtgg ctctgctgtg catgtggttc gggatctccc tgccctcgt   1680
ctacttgggc tactacttcg gcttccgaaa gcagccatat gacaaccctg tgcgcaccaa  1740
ccagattccc cggcagatcc ccgagcagcg gtggtacatg aaccgatttg tgggcatcct  1800
catggctggg atcttgccct tcggcgccat gttcatcgag ctcttcttca tcttcagtgc  1860
tatctgggag aatcagttct attacctctt tggcttcctg ttccttgttt tcatcatcct  1920
ggtggtatcc tgttcacaaa tcagcatcgt catggtgtac ttccagctgt gtgcagagga  1980
ttaccgctgg tggtggagaa atttcctagt ctccgggggc tctgcattct acgtcctggt  2040
ttatgccatc ttttatttcg ttaacaagct ggacatcgtg gagttcatcc cctctctcct  2100
ctactttggc tacacggccc tcatggtctt gtccttctgg ctgctaacgg gtaccatcgg  2160
cttctatgca gcctacatgt ttgttcgcaa gatctatgct gctgtgaaga tagactgatt  2220
ggagtggacc acgccaagc ctgctccgtc tcggacagg aagccaccct gcgtggggga  2280
ctgcaggcac gcaaaataaa ataactcctg ctcgtttgga atgtaactcc tggcacagtg  2340
ttcctggatc ctggggctgc gtgggggcg ggagggcctg tagataatct tgcgtttttc  2400
gtcatcttat tccagttctg tggggatga gtttttttgt gggttgcttt tcttcagtg   2460
ctaagaaagt tccctccaac aggaactctc tgacctgttt attcaggtgt atttctggtt  2520
tggatttttt tttccttctt tgttttaaca aatggatcca ggatggataa atccaccgag  2580
ataagggttt tggtcactgt ctccacctca gttcctcagg gctgttggcc acctatgac  2640
taactggaag aggacacgcc agagcttcag tgaggtttcc gagcctctcc ctgcccatcc  2700
tcaccactga ggccacgaca aagcacagct ccagctcgga cagcaccctc agtgccagcc  2760
agcctctgcc agacctctct ttccctcttc tccccagcct cctccagggc tgcccaaggc  2820
agggtttcca gccaggcctc ggggtcatct ttttcaccagg agcaaaccca agtcttagtt  2880
gctacaagaa aatcccctgg aagtactggg ggccaggttc cccagacagc aggaattgcc  2940
```

-continued

```
cctgttcaga gcagccggag tttgctggac cacaaggaag aagagaagag acttgcagtg    3000
aactgttttt gtgccaagaa accctggacc tggggccaag tatttcccaa gccaagcatc    3060
cacttgtctg tgtctgggaa gggatggcca aggccgctag ggtccttacc cctcaggatc    3120
actccccagc cctttcctca ggaggtaccg ctctccaagg tgtgctagca gtgggccctg    3180
cccaacttca ggcagaacag ggaggcccag agattacaga tcccctcctg taagtggcca    3240
ggcattctct ccctgccctc tctggcctct ggggtcatac tcacttcttt agccagcccc    3300
atcccctcca ccccacacct gagttcttgc ctcctccttt tggggacacc caaaacactg    3360
cttgtgagaa ggaagatgga aggtaagttc tgtcgttctt tccccaatcc ccaggaatgg    3420
acaagaagcc aacttagaaa gaagggtctc acgtggctgg cctggctcct ccgtagaccc    3480
ctgttctttt caacctctgc ccacccgtgc atgtcatcac aaacatttgc tcttaagtta    3540
caagagacca catccaccca gggattaggg ttcaagtagc agctgctaac ccttgcacca    3600
gcccttgtgg gactcccaac acaagacaaa gctcaggatg ctggtgatgc taggaagatg    3660
tccctcccct cactgcccca cattctccca gtggctctac cagcctcacc catcaaacca    3720
gtgaatttct caatcttgcc tcacagtgac tgcagcgcca agcggcatcc accaagcatc    3780
aagttggaga aagggaacc caagcagtag agagcgatat tggagtcttt tgttcattca    3840
aatcttggat ttttttttt ccctaagaga ttctcttttt aggggaatg ggaaacggac      3900 acctcataaa gggttcaaag atcatcaatt tttctgactt tttaaatcat tatcattatt    3960 attttaatt aaaaaaatgc ctgtatgcct tttttggtc ggattgtaaa taaatatacc      4020
attgtcct                                                              4028

<210> SEQ ID NO 3
<211> LENGTH: 20
<212> TYPE: DNA
<213> ORGANISM: artificial
<220> FEATURE:
<223> OTHER INFORMATION: chemically synthetized sequence
<220> FEATURE:
<221> NAME/KEY: misc_feature
<222> LOCATION: (1)..(20)

<400> SEQUENCE: 3
tgtgtgaaac aagcgccttc                                                    20

<210> SEQ ID NO 4
<211> LENGTH: 19
<212> TYPE: DNA
<213> ORGANISM: artificial
<220> FEATURE:
<223> OTHER INFORMATION: chemically synthetized
<220> FEATURE:
<221> NAME/KEY: misc_feature
<222> LOCATION: (1)..(19)
<223> OTHER INFORMATION: primer

<400> SEQUENCE: 4
atgaggtgga cgtagtagt                                                     19

<210> SEQ ID NO 5
<211> LENGTH: 26
<212> TYPE: DNA
<213> ORGANISM: artificial
<220> FEATURE:
<223> OTHER INFORMATION: chemically synthetized
<220> FEATURE:
<221> NAME/KEY: misc_feature
<222> LOCATION: (1)..(25)
<223> OTHER INFORMATION: primer
```

```
<400> SEQUENCE: 5
gaattcatgt gtgaaacaag cgcctt                                          26

<210> SEQ ID NO 6
<211> LENGTH: 24
<212> TYPE: DNA
<213> ORGANISM: artificial
<220> FEATURE:
<223> OTHER INFORMATION: chemically synthetized
<220> FEATURE:
<221> NAME/KEY: misc_feature
<222> LOCATION: (1)..(24)
<223> OTHER INFORMATION: primer

<400> SEQUENCE: 6
gtcgacagaa aaccagtgga tctg                                            24

<210> SEQ ID NO 7
<211> LENGTH: 18
<212> TYPE: DNA
<213> ORGANISM: artificial
<220> FEATURE:
<223> OTHER INFORMATION: chemically synthetized
<220> FEATURE:
<221> NAME/KEY: misc_feature
<222> LOCATION: (1)..(18)
<223> OTHER INFORMATION: primer

<400> SEQUENCE: 7
ccatggagaa ggctgggg                                                   18

<210> SEQ ID NO 8
<211> LENGTH: 20
<212> TYPE: DNA
<213> ORGANISM: artificial
<220> FEATURE:
<223> OTHER INFORMATION: chemically synthetized
<220> FEATURE:
<221> NAME/KEY: misc_feature
<222> LOCATION: (1)..(20)
<223> OTHER INFORMATION: primer

<400> SEQUENCE: 8
caaagttgtc atggatgacc                                                 20

<210> SEQ ID NO 9
<211> LENGTH: 22
<212> TYPE: DNA
<213> ORGANISM: artificial
<220> FEATURE:
<223> OTHER INFORMATION: chemically synthetized
<220> FEATURE:
<221> NAME/KEY: misc_feature
<222> LOCATION: (1)..(22)
<223> OTHER INFORMATION: primer

<400> SEQUENCE: 9
gaattcatgt gtgaaacaag cg                                              22

<210> SEQ ID NO 10
<211> LENGTH: 24
<212> TYPE: DNA
<213> ORGANISM: artificial
<220> FEATURE:
<223> OTHER INFORMATION: chemically synthetized
<220> FEATURE:
<221> NAME/KEY: misc_feature
<222> LOCATION: (1)..(24)
<223> OTHER INFORMATION: primer
```

-continued

<400> SEQUENCE: 10
gtcgatgtct atcttcacag cata                                                24

<210> SEQ ID NO 11
<211> LENGTH: 265
<212> TYPE: PRT
<213> ORGANISM: Homo sapiens
<220> FEATURE:
<221> NAME/KEY: PEPTIDE
<222> LOCATION: (1)..(265)
<223> OTHER INFORMATION: TUCAP-1 N-terminal domain, amino acids 18-282
      of TUCAP 1 protein

<400> SEQUENCE: 11

Met Cys Glu Thr Ser Ala Phe Tyr Val Pro Gly Val Ala Pro Ile Asn
1               5                   10                  15

Phe His Gln Asn Asp Pro Val Glu Ile Lys Ala Val Lys Leu Thr Ser
            20                  25                  30

Ser Arg Thr Gln Leu Pro Tyr Glu Tyr Tyr Ser Leu Pro Phe Cys Gln
        35                  40                  45

Pro Ser Lys Ile Thr Tyr Lys Ala Glu Asn Leu Gly Glu Val Leu Arg
    50                  55                  60

Gly Asp Arg Ile Val Asn Thr Pro Phe Gln Val Leu Met Asn Ser Glu
65                  70                  75                  80

Lys Lys Cys Glu Val Leu Cys Ser Gln Ser Asn Lys Pro Val Thr Leu
                85                  90                  95

Thr Val Glu Gln Ser Arg Leu Val Ala Glu Arg Ile Thr Glu Asp Tyr
            100                 105                 110

Tyr Val His Leu Ile Ala Asp Asn Leu Pro Val Ala Thr Arg Leu Glu
        115                 120                 125

Leu Tyr Ser Asn Arg Asp Ser Asp Lys Lys Lys Glu Lys Asp Val
    130                 135                 140

Gln Phe Glu His Gly Tyr Arg Leu Gly Phe Thr Asp Val Asn Lys Ile
145                 150                 155                 160

Tyr Leu His Asn His Leu Ser Phe Ile Leu Tyr His Arg Glu Asp
                165                 170                 175

Met Glu Glu Asp Gln Glu His Thr Tyr Arg Val Val Arg Phe Glu Val
            180                 185                 190

Ile Pro Gln Ser Ile Arg Leu Glu Asp Leu Lys Ala Asp Glu Lys Ser
        195                 200                 205

Ser Cys Thr Leu Pro Glu Gly Thr Asn Ser Ser Pro Gln Glu Ile Asp
    210                 215                 220

Pro Thr Lys Glu Asn Gln Leu Tyr Phe Thr Tyr Ser Val His Trp Glu
225                 230                 235                 240

Glu Ser Asp Ile Lys Trp Ala Ser Arg Val Asp Thr Tyr Leu Thr Met
                245                 250                 255

Ser Asp Val Gln Ile His Trp Phe Ser
            260                 265

<210> SEQ ID NO 12
<211> LENGTH: 15
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: amino acids 221-235 of TUCAP-1 protein

<400> SEQUENCE: 12

```
Ala Asp Glu Lys Ser Ser Cys Thr Leu Pro Glu Gly Thr Asn Ser
1               5                   10                  15

<210> SEQ ID NO 13
<211> LENGTH: 25
<212> TYPE: RNA
<213> ORGANISM: artificial
<220> FEATURE:
<223> OTHER INFORMATION: chemically synthetized
<220> FEATURE:
<221> NAME/KEY: misc_feature
<222> LOCATION: (1)..(25)
<223> OTHER INFORMATION: RNAi duplex

<400> SEQUENCE: 13
gagugacguc cagauccacu gguuu                                              25

<210> SEQ ID NO 14
<211> LENGTH: 25
<212> TYPE: RNA
<213> ORGANISM: Artificial
<220> FEATURE:
<223> OTHER INFORMATION: Chemically synthetized
<220> FEATURE:
<221> NAME/KEY: misc_feature
<222> LOCATION: (1)..(25)
<223> OTHER INFORMATION: RNA duplex

<400> SEQUENCE: 14
aaaccagugg aucuggacgu cacuc                                              25

<210> SEQ ID NO 15
<211> LENGTH: 50
<212> TYPE: PRT
<213> ORGANISM: Homo sapiens
<220> FEATURE:
<221> NAME/KEY: PEPTIDE
<222> LOCATION: (1)..(50)
<223> OTHER INFORMATION: amino acids 303-352 of TUCAP 1 protein

<400> SEQUENCE: 15

Arg Thr Leu Arg Lys Asp Ile Ala Asn Tyr Asn Lys Glu Asp Ile
1               5                   10                  15

Glu Asp Thr Met Glu Glu Ser Gly Trp Lys Leu Val His Gly Asp Val
            20                  25                  30

Phe Arg Pro Pro Gln Tyr Pro Met Ile Leu Ser Ser Leu Leu Gly Ser
        35                  40                  45

Gly Ile
    50
```